(12) United States Patent
Rittenhouse

(10) Patent No.: US 6,969,095 B2
(45) Date of Patent: Nov. 29, 2005

(54) CAPILLARY COLUMN CONNECTOR ASSEMBLY

(75) Inventor: David Rittenhouse, Fair Oaks, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 59 days.

(21) Appl. No.: 10/726,528

(22) Filed: Dec. 4, 2003

(65) Prior Publication Data

US 2004/0108718 A1 Jun. 10, 2004

Related U.S. Application Data

(63) Continuation of application No. 09/791,332, filed on Feb. 23, 2001, now Pat. No. 6,709,027.

(51) Int. Cl.$^7$ ............................................... F16L 21/06
(52) U.S. Cl. ..................... 285/332; 285/125.1; 604/283
(58) Field of Search ............................. 285/125.1, 332, 285/123.3; 604/283, 284

(56) References Cited

U.S. PATENT DOCUMENTS

| 5,540,464 | A | * | 7/1996 | Picha | ........................ | 285/332 |
| 5,578,157 | A | * | 11/1996 | Higdon | ........................ | 285/332 |
| 5,601,785 | A | * | 2/1997 | Higdon | ........................ | 285/382 |
| 2002/0117855 | A1 | * | 8/2002 | Rittenhouse | ................ | 285/332 |

* cited by examiner

*Primary Examiner*—Aaron Dunwoody

(57) ABSTRACT

A connector assembly is disclosed. The connector assembly comprises a connector having an internal conical shaped bore dimensioned so that a capillary column and auxiliary tubing can be press-fit into the bore, and an auxiliary length of cylindrical tubing having an inner diameter dimensioned so that a close fit is created when a capillary column is inserted through the auxiliary tubing and having an outer diameter dimensioned so that a fluid seal is created when the auxiliary tubing is press-fit into the bore.

3 Claims, 3 Drawing Sheets

CAPILLARY COLUMN CONNECTOR ASSEMBLY

This is a Continuation of application Ser. No. 09/791,332, filed on Feb. 23, 2001, now U.S. Pat. No. 6,709,027, the entire disclosure of which is incorporated herein by reference.

TECHNICAL FIELD

The invention relates to capillary columns used to analyze chemical substances. More specifically, the invention is directed to a new method for creating a fluid tight seal between a capillary column and a connector.

BACKGROUND ART

Chromatographic apparatus used for both gas and liquid chromatography typically employ capillary columns to provide control passageways for substances to be analyzed. Areas of analytical application for capillary columns include gas chromatography, liquid microbore chromatography, capillary electrophoresis, and supercritical fluid chromatography. In most analytical applications today, glass, metal or flexible fused silica capillary columns are used. Occasionally, polymeric capillaries are also used. Frequently, it is necessary to join two pieces of capillary columns together in order to repair a broken column, to optimize a chemical separation by joining dissimilar columns, to extend the column length, or to add retention gaps or guard columns. In most analytical applications the column ends must also be connected to a sample injector and a detector.

Connectors are known in the art for receiving a fluid stream in a first fluid-bearing conduit and then delivering the received fluid stream to a second fluid-bearing conduit. In many cases, the fluid connection is obtained by manual manipulation of separate components that comprise the connector, such as by alignment and compression of a ferrule onto a column that is fitted to a receiving device. The requirements placed upon a practical capillary connector for general use in chromatography applications are demanding. The connector must be able to withstand regular contact with chemically reactive substances and organic solvents. It must remain leak-free when operated at internal pressures ranging from zero (absolute) to several thousand pounds per square inch and over temperature cycles from sub-ambient to several hundred degrees Celsius. The thermal mass must be small and the thermal conductivity high to maintain thermal equilibrium between the column and its immediate surroundings. The dead volume in the joint must be as close to zero as possible.

Many connectors have been devised to address the need for providing a fluid tight coupling between column ends and connectors. Some connectors employ a ferrule with a conical frustrum exterior and a longitudinal bore. The column end is inserted through the bore of the ferrule and then the column-ferrule assembly is inserted into the interior of the connector. The interior of the connector is shaped to receive the ferrule. Pressure is then applied to the ferrule via a threaded fastener creating a fluid tight seal. Other connectors known as press-fit connectors consist of a hollow glass elongated tube having a conical configuration. Press-fit connectors have a tapered internal bore narrowing from the end to the central portion. In use a column end is inserted into the open end of the connector and moved into the press-fit position. Press-fit glass tubes have also been used with a ferrule and compression fitting at each end to seal against the capillary column. These methods are also used to connect the ends of two columns together with a fluid tight seal.

Known connectors provide low dead volume and chemically inert connections but suffer from several disadvantages. The ferrule and compression style connectors require several moving parts and require careful assembly. Many require separate elastomeric seals to ensure fluid-tight connection. The components used to make the seal must be chemically inert to the substances used in the analytical chromatographic process, and must exhibit good temperature stability. These components increase the cost and the complexity of the fluid seal and the connector. All of these connections show increased leakage at high temperatures, increased leakage after thermal cycling, and a sensitivity to tensions/torques applied to the fluid sealing location. The drawn conical connector of the press-fit variety has been reported to suffer from inconsistent fluid seal, particularly with modern high temperature fused silica capillary columns. At elevated temperature the fluid seal has been reported to leak and come apart.

SUMMARY OF THE INVENTION

Method and apparatus for establishing a fluid seal between capillary columns and connectors with a tapered conical internal bore is described. These methods and apparatus can be used when attaching the end of a column to an injector port or a detector. The methods and apparatus can also be used when joining two capillary columns together end to end utilizing a union connector. In addition to establishing fluid tight seals for capillary tubing, these methods and apparatus can be used on a variety of tubular objects such as on larger bore tubing such as microbore columns, and megabore columns.

The improved fluid tight seal is generally accomplished by the following steps: 1) an auxiliary length of tubing is closely fit over the outside diameter of the capillary column so that a short length of the capillary column remains exposed; 2) the capillary column is press-fit into a connector with an internal conical taper shaped bore creating a fluid seal, and; 3) the auxiliary tubing is then moved into the connector and press-fit into the conical taper section of the connector creating a second fluid seal.

One of the advantages of these methods and apparatus is that it simplifies the installation of a column into a connector. The assembly of the auxiliary length of tubing is very simple and no additional screws, ferrules or tools are required to create a fluid tight seal. The outside diameter of the auxiliary tubing need not be bonded or glued into the internal bore of the connector nor does the outside diameter of the capillary column need to be glued or bonded to the inside of the auxiliary tubing. The capillary column and auxiliary tubing are press-fit into place to create a reliable fluid seal.

When assembled, the auxiliary tubing provides an extra seal that provides several operational benefits. The increase in the fluid sealing surface area increases the stability of the fluid seal during mechanical vibration. This in turn increases the tensile force required to compromise the fluid seal which dramatically reduces the leak rate of the fluid seal. Additionally, the auxiliary tubing adds essentially no physical and thermal mass, is reliable, and is inexpensive.

DETAILED DESCRIPTION OF THE INVENTION

A simple method and apparatus for establishing a fluid seal between tubing and a connecting device that has an internal conical tapered bore is described. The method and apparatus applies to, for example, capillary columns and capillary tubing, and other tubing including microbore and megabore columns and tubing. Throughout the specification, any reference to capillary columns applies to capillary tubing, microbore and megabore columns and tubing unless otherwise noted.

The method utilizes an auxiliary length of tubing to reinforce the fluid tight seal a capillary column and a connector. Initially, the auxiliary length of tubing is "closely fit" over a capillary column. Throughout this application the phrase "closely fit" indicates that the inner diameter of the auxiliary tubing has a length or is "dimensioned" so that the capillary column can be inserted through the auxiliary tubing yet there is contact between the outer surface of the capillary column and the inner surface of the auxiliary tubing. The closeness of the fit is such that the auxiliary tubing will remain in place over the outside of the capillary column when subjected to mechanical vibration.

The end of the capillary column is inserted through the auxiliary length of tubing leaving a length of capillary column exposed. The exposed length of capillary column is long enough so that the capillary column can be inserted and press-fit into the connector without the leading edge of auxiliary tubing making contact with the internal bore of the connector. The capillary column is press-fit into a connector which has an internal conical tapered bore creating a first fluid tight seal. Subsequently, the auxiliary length of tubing is press-fit into the connector creating a second fluid tight seal.

The force during assembly deforms the auxiliary tubing such that a fluid seal is made between the leading edge of the auxiliary tubing and the taper bore of the connector. The force also presses the auxiliary tubing tight to the capillary column, creating a fluid seal between the auxiliary tubing and the capillary column. Both the first fluid seal made with the capillary tubing and the second fluid seal made with the auxiliary length of tubing are established in the internal conical tapered bore section of the connector or fitting.

Figure 1A:
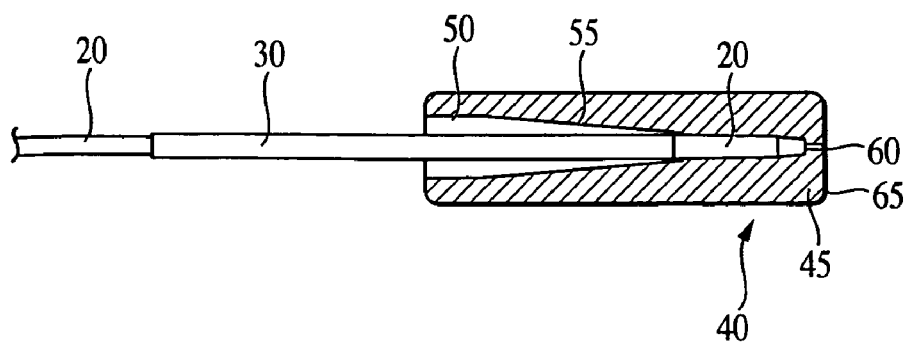
FIGS. 1A and 1B each illustrate a single connector.

FIG. 1A illustrates a sectional view of one embodiment for capillary columns. FIG. 1A shows an improved fluid tight seal consistent with this invention and accomplished by the following steps: 1) an auxiliary length of tubing 30 is closely fit over the outside diameter of a capillary column 20 so that a length of the capillary column 20 remains exposed; 2) the capillary column 20 is press-fit into a connector 40 having an internal conical taper shaped bore 55; and 3) the auxiliary tubing 30 is then moved into the connector 40 and press-fit into the conical taper shaped bore 55.

The connector 40 includes a body 45 that has a flared entry 50 at one end. The flared entry 50 narrows into a tapered conical internal bore 55. The internal bore 55 tapers to a portion 60 that has an essentially consistent diameter, which terminates at the end 65 of the body 45 of the connector 40. The body 45 is preferably fabricated of ceramic, glass, metal such as stainless steel, or polymeric materials such as PEEK. Other materials may be used so long as they are able to withstand the conditions the connector will be exposed to. The flared entry 50 has a diameter that is wide enough to facilitate insertion of the capillary column 20 and the auxiliary length of tubing 30. The tapered conical internal bore 55 is dimensioned so that a friction fit is created between the wall of the tapered conical internal bore 55 and the outer diameter of the inserted end of both the capillary column 20 and auxiliary tubing 30. The internal bore 55 extends the length of the body 45 of the connector 40 and subtends at an angle that is approximately 2 degrees. However, this is only illustrative; the length, angle, and diameter of the tapered conical bore may vary according to the type of connector being used. Examples include connectors used for microbore and megabore tubing. The diameter of the portion 60 that has an essentially consistent diameter may also vary according to the type of connector used, but it is smaller than the diameter of the capillary column 20.

The capillary column 20 is any capillary tubing including those used as columns for gas and liquid chromatography. Additionally the method of this invention encompasses tubing of larger diameter than capillary tubing. Examples of larger diameter tubing include microbore and megabore tubing.

The auxiliary length of tubing 30 is preferably formed from polyimide, but could be formed of other material and is limited only by chemical and mechanical compatibility, and intended temperature range of the seal. The internal diameter of the auxiliary length of tubing 30 and the outer diameter of the capillary column 20 have a ratio from 1/1 to 2/1. Preferably, the auxiliary tubing 30 has an internal diameter such that the capillary column 20 can be inserted into the auxiliary tubing yet the inside surface of the auxiliary tubing 30 is in contact with the outside surface of the capillary column 20. The auxiliary tubing 30 has an outer diameter such that it can be press fit into the internal bore 55.

Figure 5:
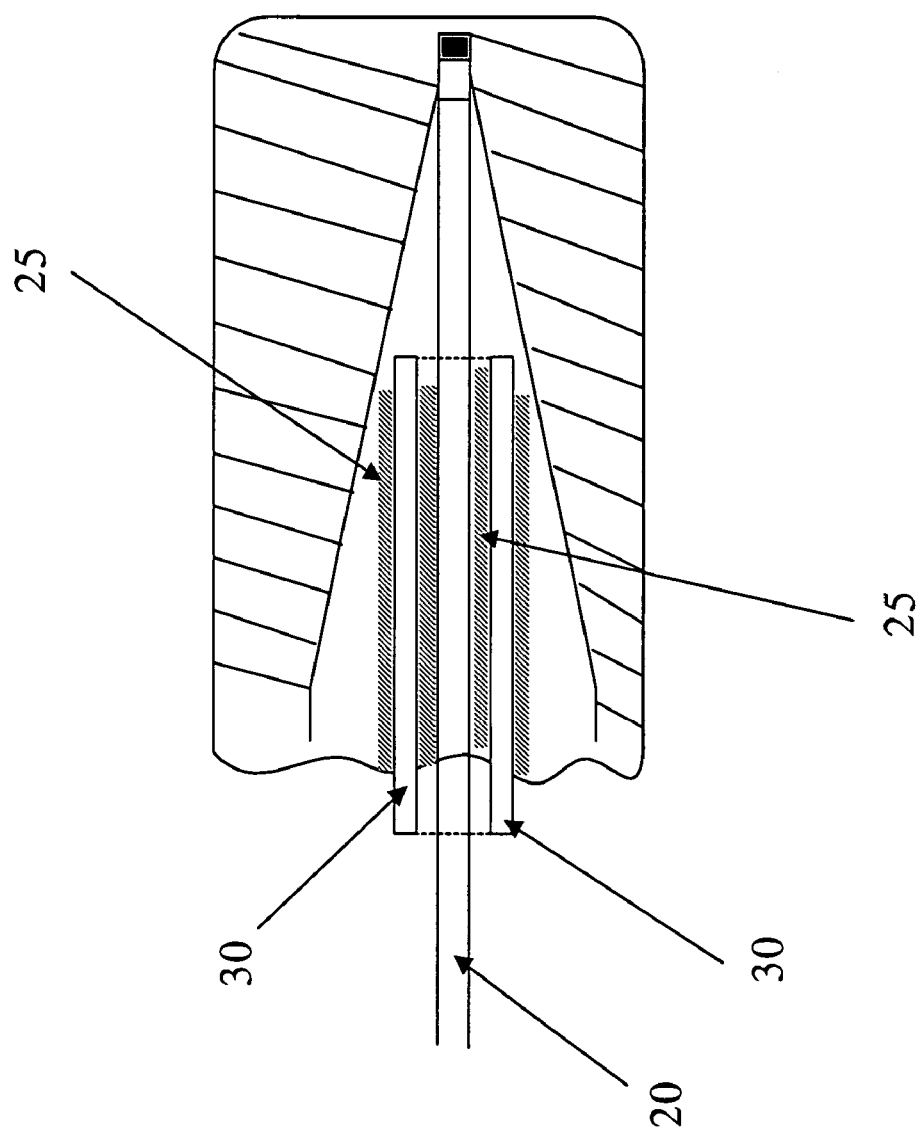
FIG. 5 depicts a single connector illustrating the addition of a bonding agent.

The outside surface of the auxiliary length of tubing 30 does not require any glue or bonding agents to create the second or secondary fluid tight seal. However, in one embodiment of the invention, the addition of a suitable bonding agent is utilized. As illustrated in FIG. 5, the bonding agent 25 is applied to the outer surface of the capillary column 20 before the auxiliary length of tubing 30 is closely fit over the capillary column 20. Alternatively, the bonding agent 25 may be applied over the outer surface of the auxiliary tubing 30 prior to being press fit into the connector 40. The addition of a bonding agent 25 will increase the strength of the fluid seal and mechanical integrity of the connection. The choice of bonding agents is limited by chemical compatibility with the tubing material, the intended temperature range, and the thermal cycling of the application. A preferred bonding agent is a polyimide resin. In yet another embodiment, the auxiliary length of tubing is constructed of partially cured material that is the same material as the capillary column 20 coating material. This method of attachment will cause the auxiliary length of tubing 30 and the capillary column 20 to cure and bond together without the addition of a bonding agent when subjected to elevated temperatures. This method also can further increase the mechanical integrity of the connection between the capillary column 20 and the auxiliary tubing 30.

Figure 1B:
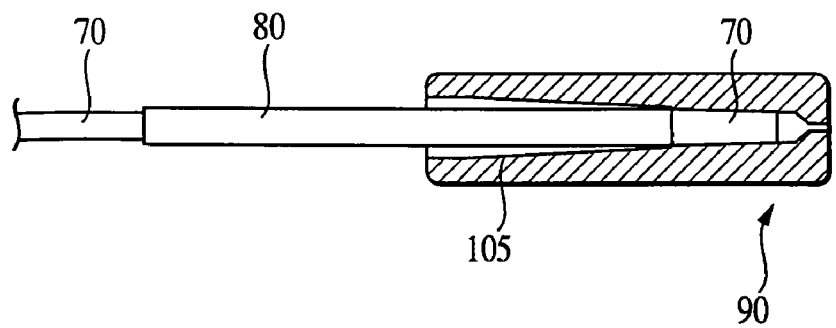
Figure 2:
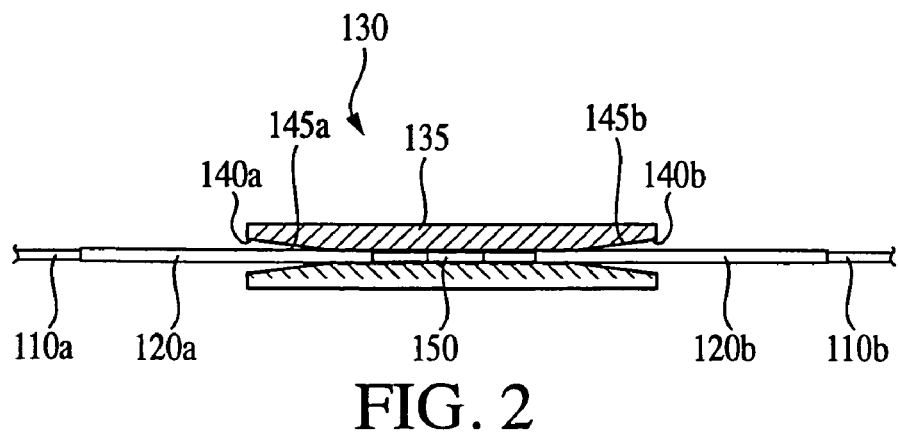
FIG. 2 depicts a press-fit glass union.
Figure 3:
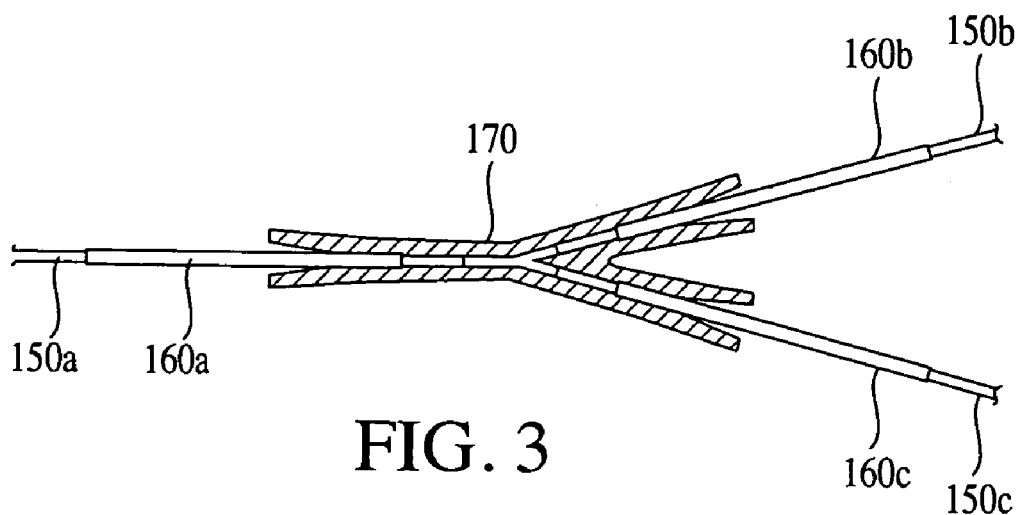
FIG. 3 depicts a three-way glass union.

FIGS. 1B, 2, and 3 illustrate other embodiments. In general, the discussion of the components in FIG. 1A applies to FIGS. 1B, 2, and 3.

FIG. 1B illustrates a sectional view of another embodiment. The components are essentially the same as in FIG. 1A except that the capillary column 20 of FIG. 1A is substituted with a megabore column 70. The megabore connector 90 is designed essentially the same as the connector 40 in FIG. 1A except that it is sized to receive a megabore column.

The auxiliary length of tubing 80 is closely fit over the outside diameter of the megabore column 70. The megabore column 70 is inserted into the megabore connector 90 and press-fit into internal conical bore 105. The auxiliary length of tubing 80 is then press-fit into the internal bore 105.

FIG. 2 illustrates the sectional view of another embodiment. FIG. 2 shows two individual capillary columns 110a and 110b each with an auxiliary length of tubing 120a and 120b closely fit over the outside diameter of the capillary columns 110a and 110b. The capillary columns 110a and 110b and the auxiliary lengths of tubing 120a and 120b are press-fit into a union connector 130.

The union connector 130, a press-fit union design, includes a body 135 that has flared entries 140a and 140b at both ends. Flared entries 140a and 140b narrow into tapered conical internal bores 145a and 145b. The internal bores 145a and 145b taper to a portion 150 of internal bore that has an essentially consistent diameter. The portion 150 of internal bore has a diameter that is smaller than the diameter of either capillary column 110a or 110b. The connector is a press fit glass union but other union designs can be used. The only required feature of a union used in this invention is that the internal bores 145a and 145b are dimensioned so that both the capillary tubes 110a and 110b and the auxiliary lengths of tubing 120a and 120b can be inserted and press-fit into the internal bores 145a and 145b.

The capillary columns 110a and 110b can be any capillary tubing; they can be identical capillary columns or different ones depending on the intended use. The capillary columns 110a and 110b can also be tubing of a larger diameter such as microbore or megabore.

The auxiliary lengths of tubing 120a and 120b operate as they do in FIGS. 1A and 1B. The internal bore of the auxiliary lengths of tubing 120a and 120b and the outside diameter of the capillary columns 110a and 110b are dimensioned so that a close fit is created between the capillary columns 110a and 110b and the auxiliary lengths of tubing 120a and 120b. The outside diameter of the auxiliary lengths of tubing 120a and 120b are dimensioned so that the auxiliary lengths of tubing 120a and 120b can be press-fit into internal bores 145a and 145b.

FIG. 3 illustrates the sectional view of another embodiment. FIG. 3 shows three individual capillary columns 150a, 150b, and 150c each with an auxiliary length of tubing 160a, 160b, and 160c closely fit over the outside diameter of the capillary columns 150a, 150b, and 150c. The capillary columns 150a, 150b, and 150c, and the auxiliary lengths of tubing 160a, 160b, and 160c, are press-fit into a 3-way press-fit union connector 170. The installation of the capillary columns 150a, 150b, and 150c are performed in the same way as in FIG. 2

Figure 4:
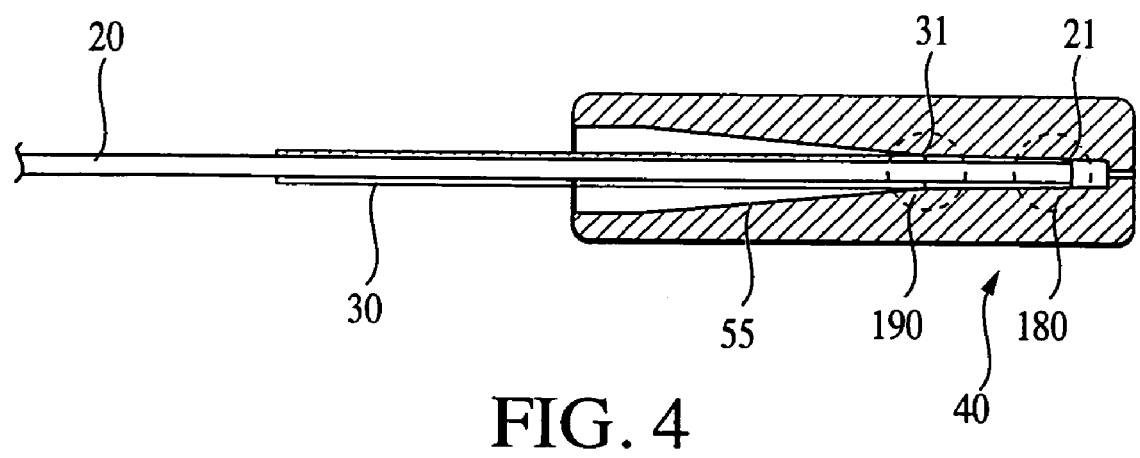
FIG. 4 depicts a single connector illustrating primary and secondary fluid seals.

FIG. 4 illustrates an enlarged sectional view of a single connector incorporating the invention. FIG. 4 illustrates the primary and secondary fluid seal of the invention. The components are the same as in FIG. 1A. The capillary column 20 is press-fit into the connector 40 creating the first or primary fluid tight seal 180. The auxiliary length of tubing 30 is subsequently press fit into the connector 40 creating the second or secondary fluid tight seal 190. Both seals are typically present in each of the embodiments shown in FIGS. 1A, 1B, 2, and 3.

Usually, the force during assembly deforms the capillary column 20 so that a fluid seal is made between the leading edge 21 of the capillary column 20 and the tapered conical internal bore 55 section of the connector 40. Additionally the force during assembly usually deforms the auxiliary length of tubing 30 so that a fluid seal is made between the leading edge 31 of the auxiliary length of tubing 30 and the tapered conical internal bore 55 section of the connector 40. The force also presses the auxiliary length of tubing 30 tight to the outside surface of the capillary column 20 creating a fluid seal between the inside surface of the auxiliary length of tubing 30 eliminating a fluid flow path between the capillary column 20 and the auxiliary length of tubing 30. Alternatively, any of the aforementioned seals may be made by a friction fit. The resulting connection has improved mechanical stability with minimal dead volume that is simple to install.

I claim:

1. A connector assembly comprising:
   a connector having a plurality of internal conical shaped bores, the connector being a three-way press-fit union;
   a plurality of capillary columns each press-fit into a respective bore creating a friction fit; and
   a plurality of auxiliary lengths of cylindrical tubing each press-fit into a respective bore created a friction fit, and having an inner diameter dimensioned so that a close fit is created when a capillary column is inserted through the auxiliary tubing and having an outer diameter dimensioned so that a fluid seal is created when the auxiliary tubing is press-fit into the bore.

2. The connector assembly of claim 1, wherein the connector and the auxiliary length of tubing are dimensioned to accommodate a megabore column.

3. The connector assembly of claim 1, wherein the connector and the auxiliary length of tubing are sized to accommodate a microbore column.

* * * * *